United States Patent [19]

Akimoto et al.

[11] Patent Number: 5,084,381
[45] Date of Patent: Jan. 28, 1992

[54] ASSAY METHOD FOR DETECTING HYDROGEN PEROXIDE

[75] Inventors: Kengo Akimoto; Sumio Asami, both of Osaka; Yukikazu Saeki, Nara, all of Japan

[73] Assignee: Suntory Limited, Osaka, Japan

[21] Appl. No.: 166,102

[22] Filed: Mar. 9, 1988

[30] Foreign Application Priority Data

Mar. 9, 1987 [JP] Japan .................. 62-53390

[51] Int. Cl.$^5$ .................. C12Q 1/60; C12Q 1/54; C12Q 1/28; C12N 9/08
[52] U.S. Cl. .................. 435/11; 435/14; 435/28; 435/192; 435/810; 435/25
[58] Field of Search .................. 435/11, 14, 25, 28, 435/911, 192, 975, 810; 436/172

[56] References Cited

U.S. PATENT DOCUMENTS

| | | | |
|---|---|---|---|
| 4,251,629 | 2/1981 | Yamanisi et al. | 435/28 |
| 4,384,042 | 5/1983 | Miike et al. | 435/11 |
| 4,416,982 | 11/1983 | Tsuda et al. | 435/11 |
| 4,592,996 | 6/1986 | Yamanishi et al. | 435/28 |
| 4,737,460 | 4/1988 | Shinmen et al. | 435/192 |

FOREIGN PATENT DOCUMENTS

| | | |
|---|---|---|
| 171074 | 2/1986 | European Pat. Off. |
| 179486 | 4/1986 | European Pat. Off. |
| 184919 | 6/1986 | European Pat. Off. |
| 200565 | 11/1986 | European Pat. Off. |
| 210449 | 2/1987 | European Pat. Off. |
| 219352 | 4/1987 | European Pat. Off. |
| 0071399 | 5/1982 | Japan .................. 435/28 |
| 0061446 | 4/1983 | Japan .................. 435/25 |
| 2079781 | 4/1987 | Japan .................. 435/910 |
| 2167421 | 11/1984 | United Kingdom. |

OTHER PUBLICATIONS

"Notifications Concerning Treaties", Industrial Property, Jan. 1988, pp. 24–30.
Akimoto et al., "Luminol Chemiluminescence Reaction Catalyzed by a Microbial Peroxidase", Analytical Biochemistry, 189 (1990), pp. 182–185.
Whitehead et al., "Enhanced Luminescence Procedure for Sensitive Determination of Peroxidase-Labelled Conjugates in Immunoassay", Nature, vol. 305 (Sep. 1983), pp. 158–159.
White et al., J. Amer. Chem. Soc., 86, 941–942, 1964.
Rauhut et al., J. Org. Chem., 31, 2431–2436, 1966.
Shevlin, J. Org. Chem., 35, 2178–2185, 1970.
Roswell Methods in Enzymology, 57, 409–423, 1978.
Merenyi et al., J. Amer. Chem. Soc., 102, 5830–5835, 1980.
Rauhut et al., Accounts Chem. Res, 2, 80–87, 1969.
Rauhut et al., J. Amer. Chem. Soc., 88, 3604–3617, 1966.
Rauhut et al., J. Amer. Chem. Soc., 89, 6515–6522, 1967.
Arakawa et al., Anal. Biochem., 97, 248–254, 1979.
Iwaoka et al., FEBS Letters, 178, 47–50, 1984.
Neufield et al., Anal. Biochem., 12, 303–309, 1965.
Pazzagli et al., Clinica Chimica Acta, 115, 277–284, 1981.
Arakawa et al., Chem. Pharm. Bull., 3036–3039, 1982.
Methods in Enzymology, vol. 133, 331, 1986.
Research Disclosure, No. 160, pp. 19–24 (Aug. 1977).

*Primary Examiner*—Esther L. Kepplinger
*Assistant Examiner*—Carol E. Bidwell
*Attorney, Agent, or Firm*—Cushman, Darby & Cushman

[57] ABSTRACT

An improved method of chemiluminescence assay for hydrogen peroxide wherein a peroxidase of microorganism origin is used in place of horseradish peroxidase. This allows an assay of unexpectedly high sensitivity to be achieved.

10 Claims, 6 Drawing Sheets

ASSAY METHOD FOR DETECTING HYDROGEN PEROXIDE

FIELD OF THE INVENTION

This invention relates to an improved assay method for detecting hydrogen peroxide, in particular an assay method the sensitivity of which is greatly improved so that the method is capable of detecting trace amounts of hydrogen peroxide without the need to use hazardous materials or an expensive apparatus.

Detection of hydrogen peroxide is becoming more and more important recently. For example, hydrogen peroxide is used in some countries as a bleaching agent for food. However, the hydrogen peroxide remaining in the food after bleaching should be substantially zero in order to prevent health hazards. Another application of hydrogen peroxide assay can be found in the clinical field. For example, there is still a demand for a simple, rapid and sensitive method of quantifying the level of a certain kind of substance, including glucose and cholesterol etc., in clinical samples such as patient's plasma. If a highly sensitive assay method for hydrogen peroxide becomes available, it will be possible to conveniently quantify such a substance in a sample by way of detecting a trace amount of hydrogen peroxide generated by an enzyme such as oxidase on said substance.

PRIOR ART

A well-known method for detecting hydrogen peroxide existing in a sample or generated there by an enzyme comprises the reaction of 4-amino-antipyrine and phenol with hydrogen peroxide in the presence of a peroxidase as a catalyst to facilitate the production of the red color of quinones, whose absorbancy is then measured by a spectrophotometer. A shortcoming of this method is that sufficient sensitivity cannot be obtained since the measurement is conducted by a spectrophotometer which detects the color produced by the reaction between the above reagent and hydrogen peroxide. Moreover, this method involves an incubation step which is needed to keep the reaction mixture at a constant temperature for producing the red color of quinones etc. Thus a considerable time is required for this assay method.

In analytical chemistry conducted in clinics, radioimmunoassay has been introduced recently as an excellent means for detecting trace substances because of its high sensitivity. However, since radioimmunoassay suffers from many safety and hygiene hazards, this assay cannot substitute for spectrophotometric analysis.

An alternative method for detecting hydrogen peroxide utilizes the chemiluminescence reaction to rapidly determine the amount of hydrogen peroxide. This chemiluminescence analysis is a well known technique and has been employed for detecting hydrogen peroxide as well as for determining the amount of fatty peroxides and is even employed in immunoassays. This method is conducted as follows when hydrogen peroxide is to be analyzed:

A luminescence reagent is added to a sample which contains hydrogen peroxide which may exist in the sample or may be generated there in situ: and the intensity of the luminescence thus produced in proportion to the amount of hydrogen peroxide is then measured. The term "luminescence reagent" as used herein refers to any single substance or a combination of substances which can react with hydrogen peroxide, especially in the presence of a peroxidase, to produce chemiluminescence. Such luminescence reagents include luminol, isoluminol etc. If the luminescence reagent is selected from luminol type compounds, the catalyst for the reaction between the reagent and hydrogen peroxide is selected from the group consisting of potassium ferrocyanide, $K_2S_2O_4$, $NaClO$, $Fe(II)$ salts, microperoxidase, peroxidase, and the like. Peroxidase is most commonly used because it eliminates the adverse effects of the background luminescence. The reaction scheme is shown as follows.

When luminol (5-amino-2,3-dihydrophthalazine-1,4-dione) and peroxidase are reacted with hydrogen peroxide, amino phthalic acid in the excited stage is produced. The mechanism of the luminescence production considered here is that this amino phtalic acid emits a light energy at 425 nm when returning to the ground stage. Luminescence analysis has the following advantages in comparison with the conventional spectrophotometric analysis:

(1) Relatively high sensitivity, which is $10^2$–$10^3$ times as high as that in spectrophotometry;
(2) Simple apparatus which affords low costs (the only essential part of an apparatus for luminescence analysis is a detector for collecting the photons and so there is no need for a light source or a spectrograph both of which are indispensable in an apparatus for spectrophotometry); and
(3) Wide dynamic range in the measurement of luminescence, which provides a linearity of the measurement extending over the luminescence intensity of $10^5$–$10^6$ orders.

One known disadvantage of the conventional chemiluminescence analysis is its generally low quantum yield which affords only a low reaction rate in comparison with that in bioluminescence analysis. Therefore, an apparatus must be equipped with an extra sensitive detector for responding to the faint light, thus the apparatus is extremely expensive in spite of its mechanical simplicity.

SUMMARY OF THE INVENTION

The object of the present invention is to provide an improved assay method for detecting hydrogen peroxide wherein the luminescence production during the assay is greatly improved, resulting in a high assay sensitivity which is preferably over ten times higher than that of the conventional assay, and most preferably over 100 times higher.

Another object of the present invention is to provide an improved assay method for detecting hydrogen peroxide wherein the need for an expensive apparatus for detecting the chemiluminescence is eliminated.

A further object of the present invention is to provide a highly sensitive assay method for detecting hydrogen peroxide wherein the hydrogen peroxide to be detected is generated in situ in a sample from a substance to be quantified by the action of an enzyme, preferably an oxidase, and the detected hydrogen peroxide level is used as the measure for the amount of the substance to be quantified.

DETAILED DESCRIPTION

It has now been discovered that when a particular peroxidase which is produced by certain microorganisms is applied in a chemiluminescence assay for hydrogen peroxide, an assay of extremely high sensitivity, which is often 100 times higher or more that of the conventional assay, can be achieved.

The peroxidase which is utilized in the method of the present invention can be obtained from a culture of peroxidase producing microorganisms. Examples of specific microorganisms preferred as the sources of peroxidase used in the present invention are those belonging to imperfect fungi or basidiomycetous fungi. A particularly preferred microorganism of imperfect fungi is *Arthromyces ramosus* which has been deposited with the Fermentation Research Institute Agency of Industrial Science and Technology under the Budapest Treaty and has been given the accession number FERM BP-838. *Arthromyces ramosus* is disclosed in Japanese Patent Laid-Open Application No. 043987/86 and U.S. Patent application Ser. No. 762,838 now U.S. Pat. No. 4,737,460 issued Apr. 12, 1988, the content of which is incorporated herein by reference. Preferred microorganisms of basidiomycetous fungi are those of genus Coprinus and particularly preferred are *Coprinus cinereus* IFO 8371, *Coprinus cinereus* IFO 30114, *Coprinus cinereus* IFO 30627, *Coprinus cinereus* IFO 30628, and *Coprinus cinereus* IFO 31333 all of which have been deposited with the Institute for Fermentation 17-85, 2-chome, Juso Honcho, Yodogawa-ku, Osaka-shi, Osaka, Japan. *Coprinus cinereus* IFO 8371 was deposited June 14, 1965. *Coprinus cinereus* IFO 30114 was deposited Feb. 10, 1976. *Coprinus cinereus* IFO 30627 was deposited Feb. 13, 1979. *Coprinus cinereus* IFO 30628 was deposited Feb. 13, 1979. *Coprinus cinereus* IFO 31333 was deposited May 10, 1983 and disclosed in Japanese Patent Laid-Open Application No. 104784/86 and U.S. Patent application Ser. No. 791,439 now abandoned, the content of which is incorporated herein by reference.

It should be understood that those people who have ordinary skill in the art will have no special difficulty in obtaining and purifying peroxidases from a culture of said microorganisms. The enzyme may be, for example, purified by a combination of several ion-exchange chromatographies. It is preferred that the enzyme is purified to such an extent that the RZ value exceeds 1.0, preferably 2.0, and the specific activity as measured by 4-amino antipyrine phenol method exceeds 50 U/mg solid, particularly 100 U/mg solid.

It is believed that the microorganisms capable of producing substantially the same peroxidase as used in the method of the invention are not limited to those listed above. Therefore, any peroxidase which is produced by a microorganism is included in the preview of the present invention as long as said peroxidase is effective for improving the assay sensitivity in a chemiluminescence assay for hydrogen peroxide. Such peroxidases will be hereafter referred to by the general term "microorganism peroxidase".

In performing the assay of the present invention, the particular reaction conditions will vary depending on the luminescence reagent used, but if luminol is used as the reagent the following conditions are preferred. An aliquot of a sample which contains hydrogen peroxide is mixed with an appropriate buffer which is slightly alkaline and preferably has a pH of about 9. A luminol solution is added thereto at a final concentration of 0.01–1 mM. A microorganism peroxidase may either be mixed in the luminol solution and added to the sample or may be separately added thereto. The peroxidase is preferably used at $2 \times 10^{-5} - 2 \times 10^{-2}$ U/ml in order to obtain accurate assay results. The mixture is then allowed to react at 10°–50° C. for 5–60 minutes. The fluorescence intensity is measured at about 425 nm. The level of hydrogen peroxide can be determined by applying the reading of the fluorescence intensity to a calibration curve which is prepared under the same conditions from a series of hydrogen peroxide solutions with known concentrations.

The sensitivity of the method is unexpectedly high. Hydrogen peroxide can be detected in amounts as low as 10 p mol/ml. This sensitivity is expected to be raised more by selecting appropriate conditions. The method also has an advantageously wide dynamic range which extends to the order of well over $10^3$.

It may be readily understood by a skilled person that the important aspect of the method of the present invention is the fact that a microorganism peroxidase is used in place of horseradish peroxidase in a chemiluminescence assay for detecting hydrogen peroxide. Therefore, the method of the invention may be carried out with various alterations or modifications without departing from the scope of the invention. For example, the chemiluminescence assay may be performed by the stopped flow method. All such modifications or alterations are intended to be included in the embodiments of the present invention. It should also be understood that the hydrogen peroxide to be detected may be one generated in situ from a substance in a sample by the action of an oxidase enzyme, which is preferably specific to said substance, whereby the amount of said substance is determined indirectly. Examples of such substances capable of generating hydrogen peroxide by an oxidase are glucose, cholesterol, uric acid, etc.

The invention will be explained in more detail by referring to the following experiment and non-limiting examples.

EXPERIMENT

Figure 2:
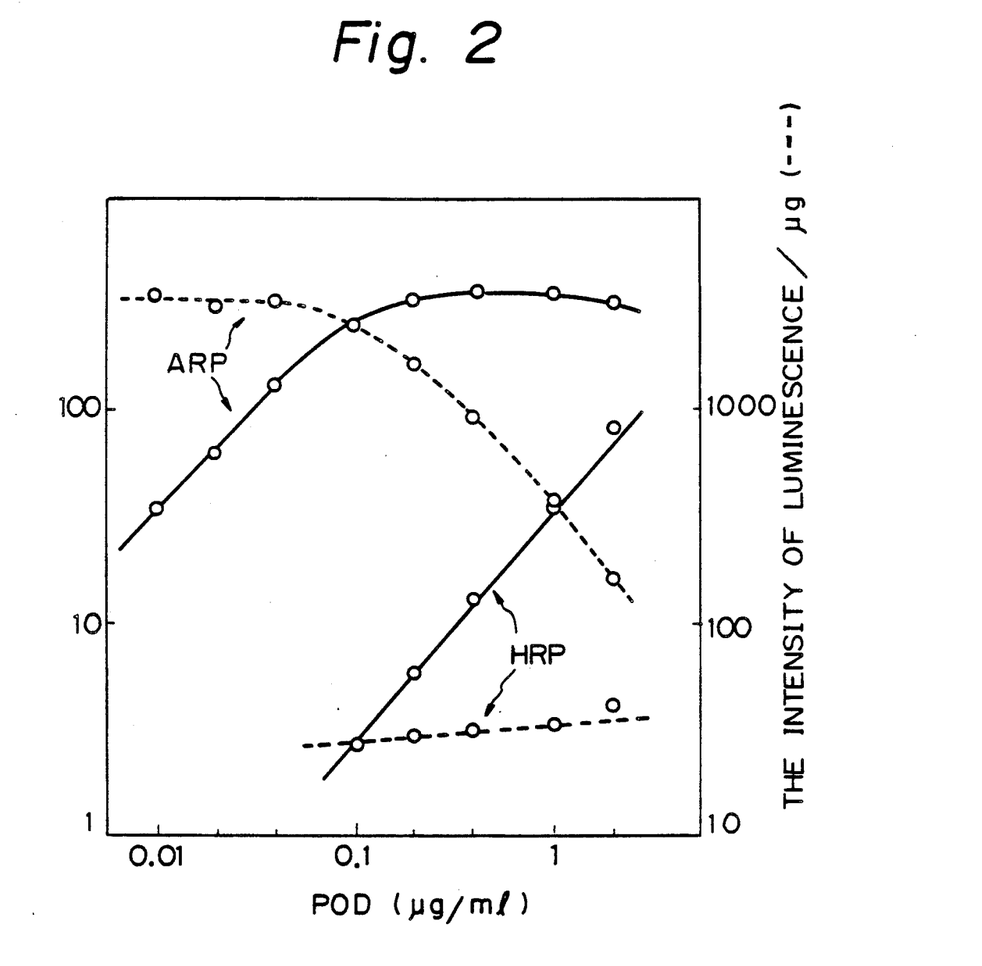
FIG. 2 represents the relations of luminescence intensity versus peroxidase concentration in the assay method of the present invention and the conventional assay method respectively. The solid lines represent total luminescence versus peroxidase concentration while the broken lines represent luminescence per unit of peroxidase versus peroxidase concentration.

An experiment was conducted to ascertain the efficacy of a microorganism peroxidase in improving the sensitivity of a chemiluminescence assay for detecting hydrogen peroxide and at the same time to determine the preferred rate of said peroxidase to be used in the assay of the invention. The concentration of hydrogen peroxide was kept constant and the amount of the enzyme was varied. 700 μl of 1 mM luminol solution in a 50 mM pyrophosphate buffer containing ARP (2 μg/ml-0.01 μg/ml) or HRP (2.2 μg/ml-0.04 μg/ml) was prepared. To this solution was added 100 μl of hydrogen peroxide solution (10 μM) in a pyrophosphate buffer (50 mM, pH 9.0). The intensity of chemiluminescence was then measured. The total amounts, as well as the amount per 1 μg of peroxidase, of the chemiluminescence produced were plotted in FIG. 2. Referring to the solid line for ARP in FIG. 2, the ARP produced a greater amount of chemiluminescence at the higher concentrations. However, the reaction was too rapid at the higher ARP level for a luminescence photometer to collect all of the chemiluminescence emitted so that the amount of chemiluminescence detected per unit of ARP decreased even though a greater total amount of chemiluminescence was observed. On the other hand, a constant chemiluminescence emission per unit of ARP was observed at a lower ARP range even though the total chemiluminescence emission decreased. Therefore, an excellent dose dependent correlation between the total amount of chemiluminescence and the amount of ARP could be established. suggesting that this assay was particularly suitable for detecting a very low level of hydrogen peroxide. Moreover, the results in FIG. 2 show that the sensitivity in this chemiluminescence assay using a microorganism peroxidase was about 100 times as high as that achieved by the conventional assay where HRP was used.

EXAMPLE 1

A calibration curve for detecting hydrogen peroxide in accordance with the assay method of the invention was prepared and the sensitivity of the assay was compared with that of the conventional chemiluminescence assay in which horseradish peroxidase is used.

To 700 μl of hydrogen peroxide solution (100 μM-0.01 μM) in a 50 mM pyrophosphate buffer (pH 9.0) was added luminol solution (1 mM) containing ARP (2 μg/ml), CCP (3 μg/ml) or HRP (2.2 μg/ml) in 100 μl of a 50 mM pyrophosphate buffer (pH 9.0), respectively, and the intensity of luminescence emitted was measured by a luminescence photometer (Lumac ® BIOCOUNTER M2010, 3M, Pharma. Co.) The concentration of the respective enzymse was determined based on the heme content as measured by the absorbancy at 403 nm.

Figure 1:
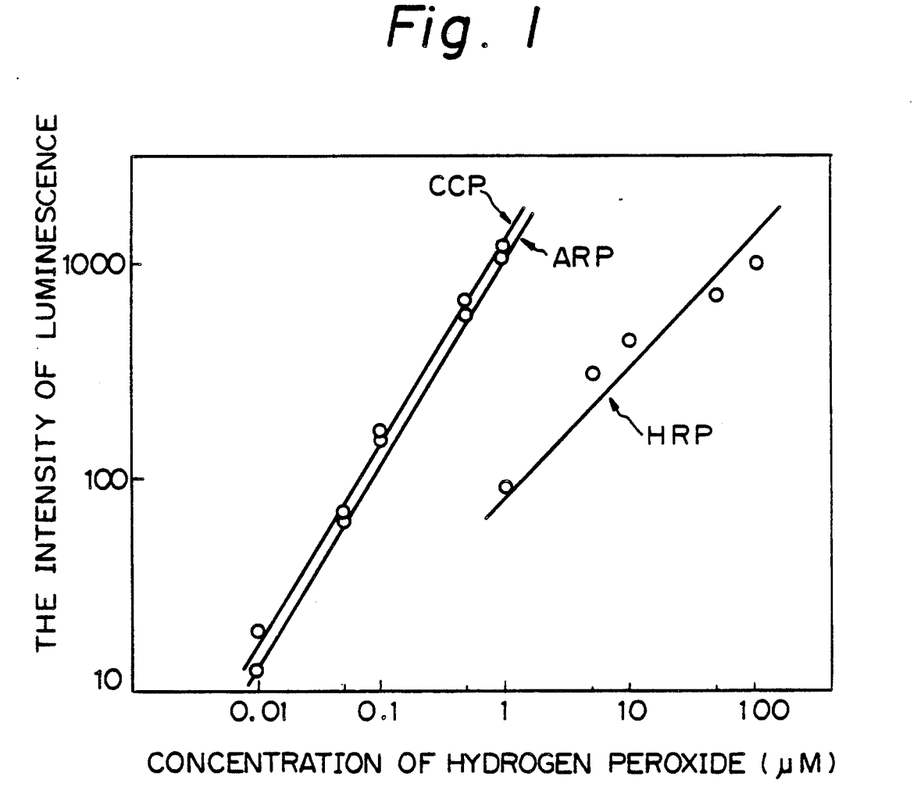
FIG. 1 represents calibration curves showing the superior sensitivity of the assay method of the present invention using a microorganism peroxidase over the conventional chemiluminescence assay wherein horseradish peroxidase is used.

The results are shown in FIG. 1. The method of the invention which uses a microorganism peroxidase (i.e. ARP or CCP) showed a good dose dependent correlation between the concentration of hydrogen peroxide to be assayed and the luminescence intensity, while the conventional method which uses horseradish peroxidase did not show a sufficiently sharp dose dependent relationship. In addition, the luminescence produced by the two microorganism peroxidases was 30 times as strong as that produced by horseradish peroxidase. Consequently, the method of the invention which utilizes a peroxidase of microorganism origin provides a higher sensitivity and accuracy as compared with the conventional chemiluminescence assay for detecting hydrogen peroxide existing or artificially generated in a sample.

EXAMPLE 2

The luminescence intensities produced by ARP and HRP were compared in the stopped-flow method. The hydrogen peroxide measured in this example was generated from glucose or cholesterol in the sample by the action of glucose oxidase (100 U/mg, commercially available from Toyobo Co., Japan) or cholesterol oxidase (5 U/mg, commercially available from Amano Pharma. Co., Japan) respectively. More specifically, 200 μl of glucose oxidase solution (2.6 mg/ml) was added to a mixture comprising 60 μl of glucose solution (10 mM) and 1 ml of phosphate buffer (50 mM, pH 7.0). The resulting mixture was allowed to react at 37° C. for 5 minutes and a 1 ml aliquot of the mixture was added to 9 ml of a pyrophosphate buffer (50 mM, pH 9.0) to terminate the reaction. On the other hand, 400 μl of cholesterol oxidase solution (2.3 mg/ml) was added to a mixture comprising 240 μl of cholesterol solution (100 μg/ml) and 2 ml of a phosphate buffer (10 mM, pH 7.0) containing 0.05% of Triton X-100. The resulting mixture was reacted at ambient temperature for 10 minutes. A 2 ml aliquot of the reacted solution was mixed with 8 ml of pyrophosphate buffer solution (50 mM, pH 9.0) to terminate the reaction.

Figure 3:
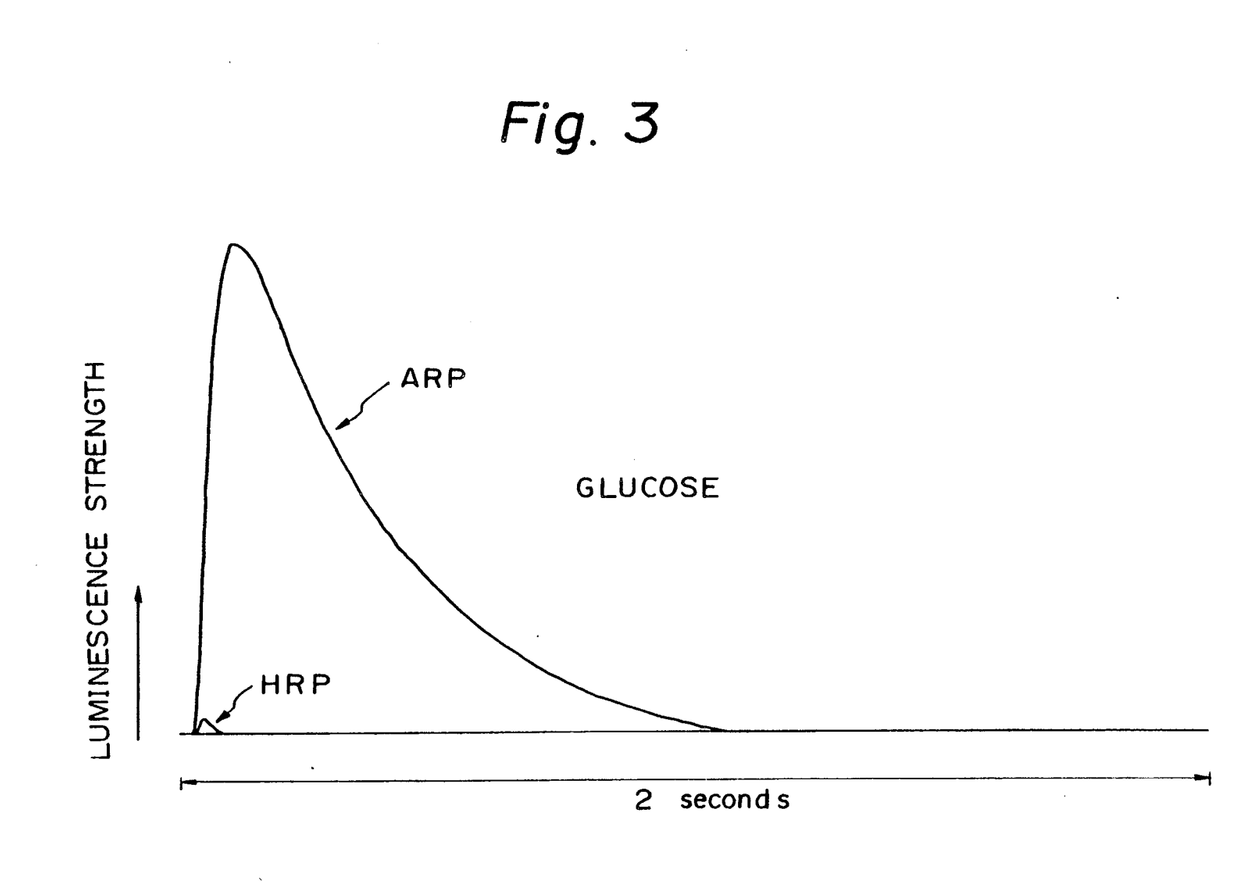
FIG. 3 compares the results of the luminescence intensity between ARP and HRP in the measurement of hydrogen peroxide from the glucose solution.
Figure 4:
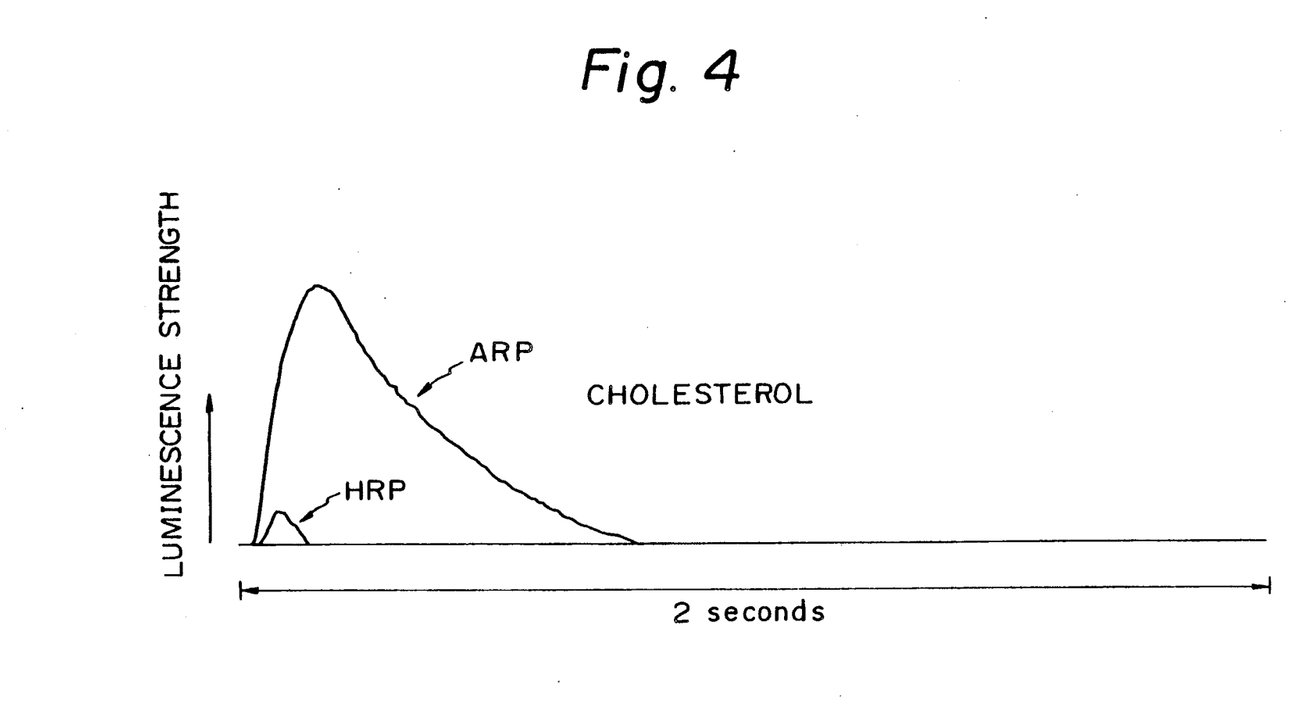
FIG. 4 compares the results of the luminescence intensity between ARP and HRP in the measurement of hydrogen peroxide from the cholesterol solution.

The sample which contained hydrogen peroxide produced by the enzyme action as described above was mixed with luminol (1 mM) in a pyrophosphate buffer (50 mM, pH 9.0) containing ARP at 50 μg/ml or HRP at 55 μg/ml, and the luminescence intensity was measured by a stopped-flow photometer (Yunion Giken Co., Japan: Type RA-401). FIG. 3 compares the results of the luminescence intensity between ARP and HRP in the measurement of hydrogen peroxide from the glucose solution and FIG. 4 compares those from the cholesterol solution. As can be clearly seen, the luminescence intensity achieved by ARP was stronger than that attained by HRP; that is, stronger by 49 times in the case of cholesterol, and as much as 365 times higher in the case of glucose.

The above results strongly indicate the superiority of the microorganism peroxidase over horseradish peroxidase in a chemiluminescence assay for hydrogen peroxide.

EXAMPLE 3

Figure 5:
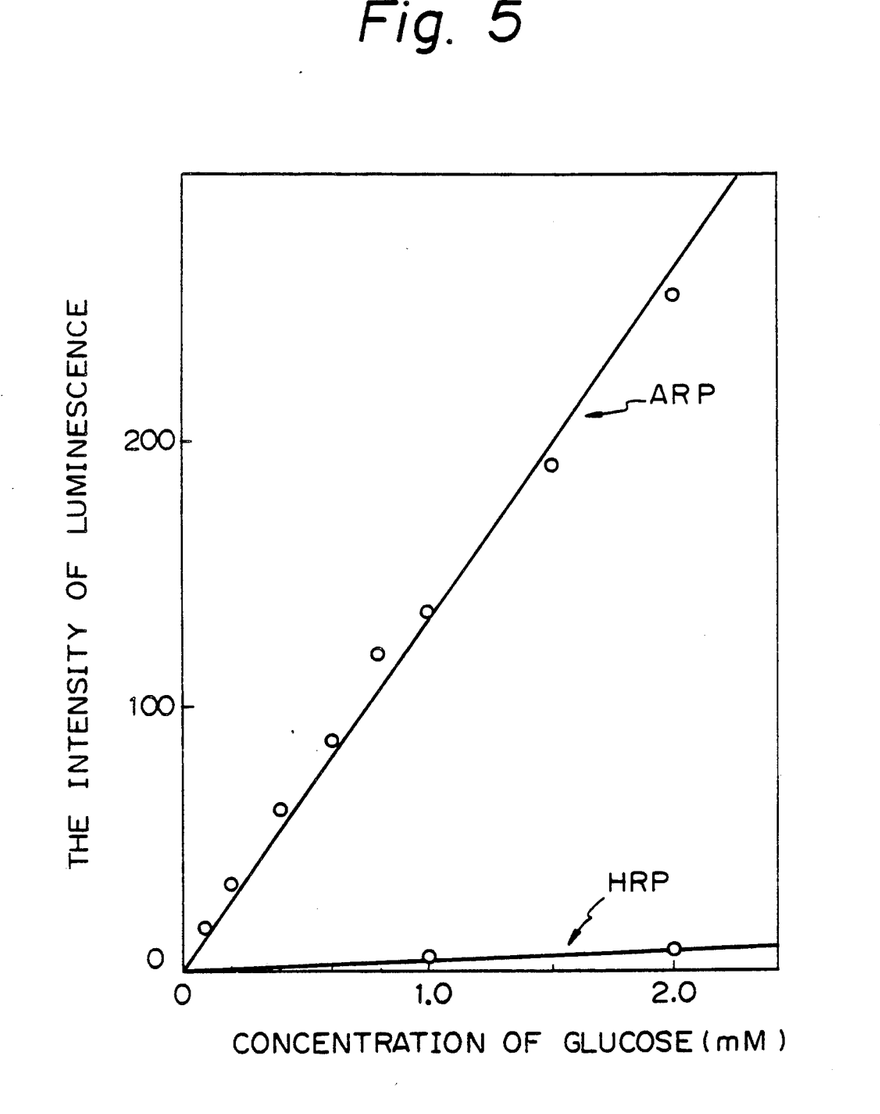
FIG. 5 represents two calibration curves of glucose concentration versus luminescence intensity measured by the luminescence photometer which detected hydrogen peroxide produced from glucose solutions of varying concentrations. The upper line was obtained by the method of the invention using ARP and the lower line was obtained by the conventional method using HRP.

Glucose solutions at various concentrations were prepared and 60 μl of each of said solutions was mixed with 1 ml of a phosphate buffer (50 mM, pH 7.0). To this solution was added 200 μl of glucose oxidase solution (2.6 mg/ml) and the resulting mixture was allowed to react at 37° C. for 5 minutes. A 1 ml aliquot of the reacted solution was added to 9 ml of a pyrophosphate buffer (50 mM, pH 9.0) to terminate the reaction. A 700 μl aliquot was pipetted from the reacted solution and mixed with 100 μl of luminol solution (1 mM) in pyrophosphate buffer (50 mM, pH 9.0) containing either ARP (2 μg/ml) or HRP (2.2 μg/ml). The luminescence intensity thus produced was measured by a luminescence photometer and the results were expressed as two calibration curves as shown in FIG. 5. The results show that the luminescence produced by ARP was 28 times as strong as that achieved by HRP, suggesting the great suitability of ARP for the highly sensitive chemiluminescence analysis of hydrogen peroxide.

EXAMPLE 4

Figure 6:
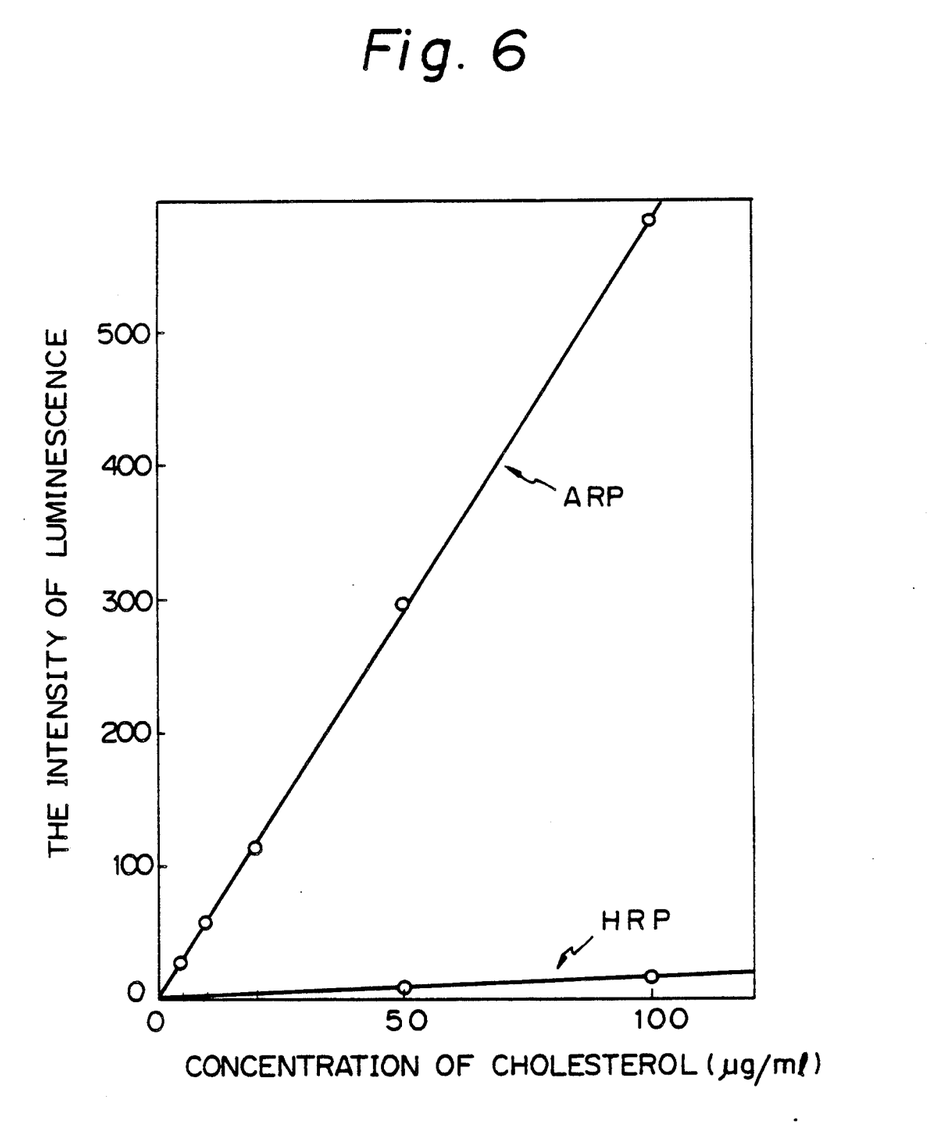
FIG. 6 represents two calibration curves of cholesterol concentration versus luminescence intensity measured by the luminescence photometer which detected hydrogen peroxide produced from cholesterol solutions of varying concentrations. The upper line was obtained by the method of the invention using ARP and the lower line was obtained by the conventional method using HRP.

Cholesterol solutions at various concentrations were prepared and 120 μl of each of said solutions was mixed with 1 ml of a phosphate buffer (10 mM, pH 7.0) containing Triton X-100 at 0.05%. To this solution was added 200 μl of cholesterol oxidase solution (0.2 mg/ml) and the resulting mixture was allowed to react at 37° C. for 15 minutes. A 1 ml aliquot of the reacted solution was added to 4 ml of a pyrophosphate buffer (50 mM, pH 9.0) and the reaction was terminated. A 700 μl aliquot was pipetted from the reacted solution and mixed with 100 μl of luminol solution (1 mM) in a pyrophosphate buffer (50 mM, pH 9.0) containing either ARP (2 μg/ml) or HRP (2.2 μg/ml). The luminescence intensity thus produced was measured by a luminescence photometer and the results were expressed as two calibration curves as shown in FIG. 6. The results show that the luminescence produced by ARP was 134 times as strong as that attained by HRP, suggesting the great suitability of ARP for the highly sensitive chemiluminescence analysis of hydrogen peroxide.

The foregoing examples evidence the fact that the luminescence produced by microorganism peroxidase is well over 100 times as strong as that produced by horseradish peroxidase. Accordingly, the method of the invention provides a successful chemiluminescence analysis without needing an extra-sensitive luminescence photometer as has been needed in the conventional chemiluminescence analysis of hydrogen peroxide.

The assay method of the present invention may be applied to the enzyme immunoassay also. Taking the sandwich assay as a typical enzyme immunoassay, for example, a substance to be quantitated (such as insulin) in a sample is reacted with first anti-insulin antibody which has been immobilized on the inner wall surface of a container. The container is then washed with an appropriate medium such as PBS and second anti-insulin antibody which has been labelled with a peroxidase (POD) is added thereto. The container is washed again and a known amount of $H_2O_2$ is added followed by luminescence reagent, whereby the emission of luminescence will take place. The intensity of the luminescence will be proportional to the amount of the POD attached on the container surface. Now referring to FIG. 2, microorganism peroxidase has a higher sensitivity than horseradish peroxidase. This means that the assay method of the invention avoids, when applied to the enzyme immunoassay, excessive use of the valuable enzyme.

What is claimed is:

1. An assay method for detecting hydrogen peroxide in a sample comprising contacting said sample a luminescence reagent in the presence of a peroxidase produced by a microorganism capable of producing peroxidase selected from the group consisting of *Arthromyces ramosus* and *Coprinus cinereus*, and determining the resulting chemiluminescence as the measure of the hydrogen peroxide level in the sample.

2. A method according to claim 1 wherein *Arthromyces ramosus* has the accession number FERM BP-838.

3. A method according to claim 1 wherein said microorganism is *Coprinus cinereus* IFO 8371, *Coprinus cinereus* IFO 30114, *Coprinus cinereus* IFO 30627, *Coprinus cinereus* IFO 30628 or *Coprinus cinereus* IFO 31333.

4. A method according to claim 1 wherein said assay method is capable of detecting hydrogen peroxide at least at the level of 10 p mol/ml.

5. A method according to claim 1 wherein the hydrogen peroxide to be detected is produced in situ in the sample by the action of an oxidase enzyme on a substance contained in said sample.

6. A method according to claim 5 wherein said substance which is subjected to the action of the enzyme is selected from the group consisting of glucose and cholesterol.

7. A kit for assaying hydrogen peroxide in a sample which comprises:
   a) luminol;
   b) peroxidase produced by a microorganism which produces peroxidase selected from the group consisting of *Arthromyces ramosus* and *Coprinus cinereus;* and
   c) a buffer component for providing a convenient pH condition when said luminol is reacted with hydrogen peroxide in said sample to cause the emission of chemiluminescence in the presence of said peroxidase.

8. A kit according to claim 7 wherein said components a), b) and c) are packed in separate containers.

9. In an assay for detecting a peroxidase level in a sample by contacting said sample with a luminescence reagent in the presence of a predetermined amount of hydrogen peroxide and determining the resulting chemiluminescence as the measure of the peroxidase level in the sample, wherein the improvement comprises that the peroxidase to be detected is produced by a microorganism capable of producing peroxidase selected from the group consisting of *Arthromyces ramosus* and *Coprinus cinereus.*

10. An assay according to claim 9 wherein said peroxidase level of at least 0.01 μl/ml can be detected.

* * * * *